United States Patent
Al-Tawil

(10) Patent No.: US 8,961,437 B2
(45) Date of Patent: Feb. 24, 2015

(54) MOUTH GUARD FOR DETECTING AND MONITORING BITE PRESSURES

(76) Inventor: Youhanna Al-Tawil, Knoxville, TN (US)

(*) Notice: Subject to any disclaimer, the term of this patent is extended or adjusted under 35 U.S.C. 154(b) by 379 days.

(21) Appl. No.: 13/358,216

(22) Filed: Jan. 25, 2012

(65) Prior Publication Data

US 2012/0123225 A1    May 17, 2012

Related U.S. Application Data

(63) Continuation-in-part of application No. 13/092,234, filed on Apr. 22, 2011, now Pat. No. 8,579,766, and a continuation-in-part of application No. 12/782,356, filed on May 18, 2010, now Pat. No. 8,047,964, which is a continuation-in-part of application No. 12/556,237, filed on Sep. 9, 2009, now Pat. No. 7,942,782.

(51) Int. Cl.
| | |
|---|---|
| A61B 5/103 | (2006.01) |
| A61B 5/0205 | (2006.01) |
| G06F 3/01 | (2006.01) |
| A61B 5/00 | (2006.01) |
| A61B 5/22 | (2006.01) |
| G05G 1/52 | (2008.04) |

(52) U.S. Cl.
CPC .............. G06F 3/011 (2013.01); A61B 5/4542 (2013.01); A61B 5/228 (2013.01); G05G 1/52 (2013.01)
USPC ........................................................ 600/590

(58) Field of Classification Search
CPC ...... A61B 5/224; A61B 5/228; A61B 5/4542; A61B 5/4547; A61B 5/4552; A61B 5/4557; A61B 19/045; G05G 1/52; G06F 3/011
USPC .......................................................... 600/590
See application file for complete search history.

(56) References Cited

U.S. PATENT DOCUMENTS

| | | | |
|---|---|---|---|
| 4,379,615 A * | 4/1983 | Toda et al. .................... | 385/147 |
| 4,408,192 A | 10/1983 | Ward et al. | |
| 4,562,432 A | 12/1985 | Sremac | |
| 4,567,479 A | 1/1986 | Boyd | |
| 4,629,424 A | 12/1986 | Lauks et al. | |
| 4,697,601 A | 10/1987 | Durkee et al. | |
| 4,746,913 A | 5/1988 | Volta | |
| 4,758,829 A | 7/1988 | Smith, III | |

(Continued)

OTHER PUBLICATIONS

Y. Takahashi, et al., High-speed Pressure Sensor Grid for Humanoid Robot Foot, IEEE/IROS (2005).
Pressure Mapping Systems article, http://www.sensorland.com/HowPage033.html (May 22, 2008) (7 pages).
Pressure Transducers article, http://www.omega.com/prodinfo/pressuretransducers.html (May 27, 2008) (3 pages).

(Continued)

*Primary Examiner* — Sean Dougherty
*Assistant Examiner* — Michael C Stout
(74) *Attorney, Agent, or Firm* — Peter L. Brewer; Baker Donelson

(57) ABSTRACT

An intra-oral pressure monitoring system is provided. The system is beneficial for measuring or monitoring teeth clinching or grinding during sleep. The system includes a generally horseshoe-shaped, elastomeric mouth piece. The mouth piece is dimensioned to reside between the upper and lower teeth of a patient. The mouth piece has a two or more fluid-containing cells embedded therein. The cells are configured to receive pressure applied by the teeth of a patient. The system is able to monitor bite pressures during a patient's sleep or time of resting. A method for monitoring bite pressures of a patient during sleep is also provided.

37 Claims, 6 Drawing Sheets

(56) References Cited

U.S. PATENT DOCUMENTS

| | | | |
|---|---|---|---|
| 4,783,656 A | 11/1988 | Katz et al. | |
| 4,856,993 A * | 8/1989 | Maness et al. | 433/68 |
| 4,865,610 A | 9/1989 | Muller | |
| 4,976,618 A * | 12/1990 | Anderson | 433/215 |
| 4,997,182 A | 3/1991 | Kussick | |
| 5,212,476 A | 5/1993 | Maloney | |
| 5,213,553 A | 5/1993 | Light | |
| 5,422,640 A | 6/1995 | Haley | |
| 5,452,727 A | 9/1995 | Tura et al. | |
| 5,460,186 A | 10/1995 | Buchhold | |
| 5,523,745 A | 6/1996 | Fortune et al. | |
| 5,609,161 A | 3/1997 | Tura et al. | |
| 5,689,246 A | 11/1997 | Dordick et al. | |
| 5,819,893 A * | 10/1998 | Wagner et al. | 191/12.4 |
| 5,830,235 A | 11/1998 | Standley | |
| 5,904,140 A | 5/1999 | McGoogan | |
| 5,954,673 A | 9/1999 | Staehlin et al. | |
| 5,995,855 A * | 11/1999 | Kiani et al. | 600/310 |
| 6,033,367 A | 3/2000 | Goldfield | |
| 6,050,961 A | 4/2000 | Arnold | |
| 6,077,108 A * | 6/2000 | Lorscheider et al. | 439/501 |
| 6,089,864 A * | 7/2000 | Buckner et al. | 433/71 |
| 6,108,592 A | 8/2000 | Kurtzberg et al. | |
| 6,190,335 B1 | 2/2001 | Howard et al. | |
| 6,222,524 B1 | 4/2001 | Salem et al. | |
| 6,325,665 B1 * | 12/2001 | Chung | 439/501 |
| 6,327,507 B1 * | 12/2001 | Buchan | 607/115 |
| 6,424,551 B1 * | 7/2002 | Lin | 363/146 |
| 6,430,450 B1 | 8/2002 | Bach-y-Rita et al. | |
| 6,452,108 B1 * | 9/2002 | Major | 174/135 |
| 6,472,617 B1 * | 10/2002 | Montagnino | 177/126 |
| 6,511,441 B1 | 1/2003 | Wakumoto et al. | |
| 6,633,770 B1 * | 10/2003 | Gitzinger et al. | 455/575.1 |
| 6,679,448 B1 * | 1/2004 | Carpenter et al. | 242/385.3 |
| 6,702,765 B2 | 3/2004 | Robbins et al. | |
| 6,771,190 B2 | 8/2004 | Gordon | |
| 6,801,231 B1 | 10/2004 | Beltz | |
| 6,833,786 B1 | 12/2004 | Sun et al. | |
| 6,893,406 B2 | 5/2005 | Takeuchi et al. | |
| 6,897,788 B2 | 5/2005 | Khair et al. | |
| 6,971,993 B2 | 12/2005 | Fletcher | |
| 7,020,508 B2 * | 3/2006 | Stivoric et al. | 600/390 |
| 7,057,889 B2 * | 6/2006 | Mata et al. | 600/301 |
| 7,071,844 B1 | 7/2006 | Moise | |
| 7,127,270 B2 | 10/2006 | Sinclair | |
| 7,768,499 B2 | 8/2010 | Sturtz | |
| 7,942,782 B2 * | 5/2011 | Al-Tawil | 482/1 |
| 7,993,275 B2 * | 8/2011 | Banet et al. | 600/485 |
| 7,995,031 B2 | 8/2011 | Manual | |
| 8,040,858 B2 | 10/2011 | Muhamed et al. | |
| 8,044,766 B2 | 10/2011 | Ghovanloo et al. | |
| 8,046,491 B2 | 10/2011 | Klein et al. | |
| 8,047,964 B2 * | 11/2011 | Al-Tawil | 482/1 |
| 2003/0016817 A1 * | 1/2003 | Koester et al. | 379/430 |
| 2003/0078521 A1 * | 4/2003 | Robbins et al. | 600/587 |
| 2003/0184521 A1 * | 10/2003 | Sugita | 345/163 |
| 2003/0192760 A1 * | 10/2003 | Burke et al. | 191/12.4 |
| 2003/0209397 A1 * | 11/2003 | Reindle et al. | 191/12.2 R |
| 2003/0220579 A1 * | 11/2003 | Mault | 600/531 |
| 2004/0002665 A1 * | 1/2004 | Parihar et al. | 600/587 |
| 2004/0024284 A1 * | 2/2004 | Kindlein et al. | 600/3 |
| 2004/0114313 A1 * | 6/2004 | Mata et al. | 361/679 |
| 2004/0136552 A1 * | 7/2004 | Bendixen et al. | 381/306 |
| 2004/0149533 A1 * | 8/2004 | Milano | 191/12.4 |
| 2004/0256188 A1 * | 12/2004 | Harcourt | 191/12.2 A |
| 2005/0148898 A1 * | 7/2005 | Odderson | 600/544 |
| 2005/0171451 A1 * | 8/2005 | Yeo et al. | 600/547 |
| 2006/0028198 A1 * | 2/2006 | Hoopengarner | 324/157 |
| 2006/0122555 A1 * | 6/2006 | Hochman | 604/67 |
| 2007/0016957 A1 * | 1/2007 | Seaward et al. | 726/26 |
| 2007/0197923 A1 * | 8/2007 | Kishimoto et al. | 600/490 |
| 2008/0080732 A1 * | 4/2008 | Sneed | 381/374 |
| 2009/0156967 A1 * | 6/2009 | Cohen | 600/590 |
| 2009/0270759 A1 * | 10/2009 | Wilson et al. | 600/561 |
| 2010/0069200 A1 * | 3/2010 | Al-Tawil | 482/1 |
| 2010/0204614 A1 * | 8/2010 | Lindquist et al. | 600/586 |
| 2010/0249630 A1 * | 9/2010 | Droitcour et al. | 600/529 |
| 2011/0057874 A1 | 3/2011 | Al-Tawil | |
| 2011/0125063 A1 * | 5/2011 | Shalon et al. | 600/590 |
| 2011/0287392 A1 | 11/2011 | Al-Tawil | |
| 2012/0046572 A1 * | 2/2012 | Odderson | 600/554 |

OTHER PUBLICATIONS

Piezoelectric Sensor article, http://en.wikipedia.org/wiki/Piezoelectric$_{13}$ sensor (May 27, 2008) (5 pages).

ASDX Sensors, brochure, www.honeywell, com/sensing (Sep. 28, 2009) (4 pages).

Adult Pacifier article, http://www.diaperconnection.com/pacifier.html (Sep. 28, 2009) (3 pages).

D. Koc. A. Dogan, and B. Bek, Bite Force and Influential Factors on Bite Force Measurements: A Literature Review, European Journal of Dentistry (Apr. 2010) (12 pages).

* cited by examiner

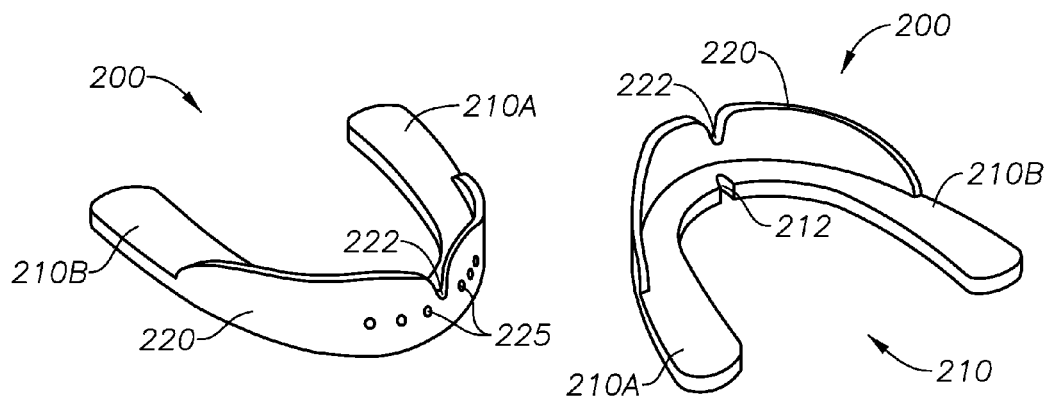
Fig. 2A
Fig. 2B
Fig. 2C
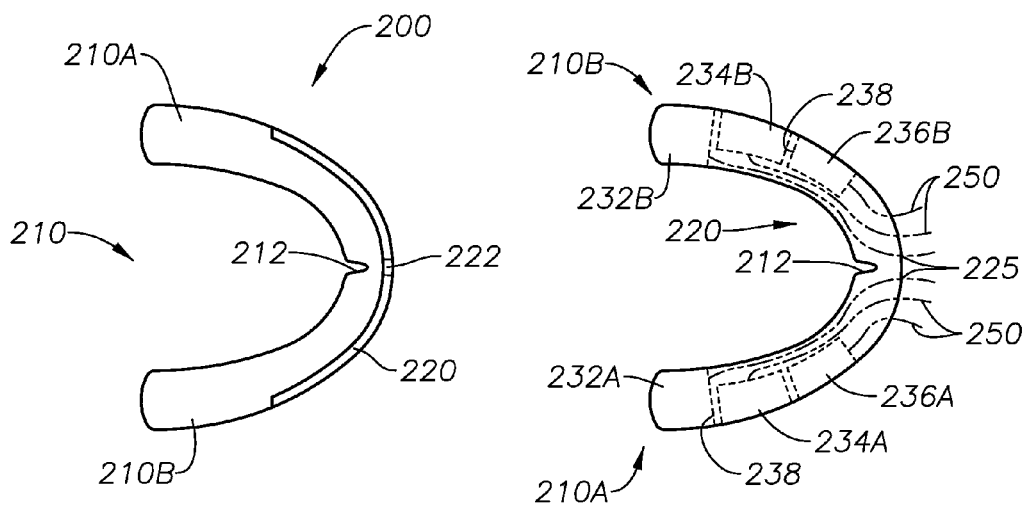
Fig. 2D
Fig. 2E

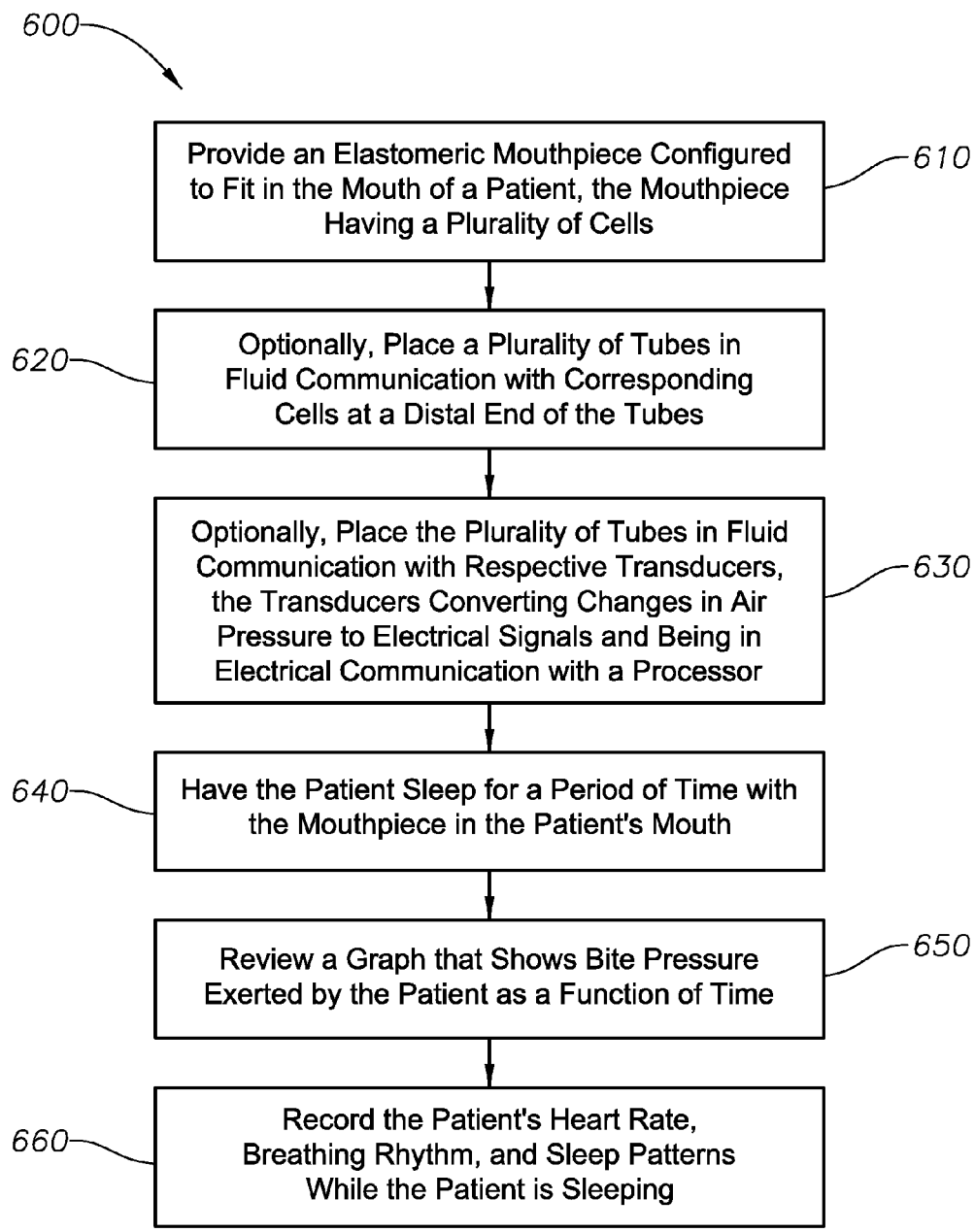

MOUTH GUARD FOR DETECTING AND MONITORING BITE PRESSURES

CROSS REFERENCE TO RELATED APPLICATIONS

This application is a continuation-in-part of a non-provisional patent application bearing U.S. Ser. No. 13/092,234 filed 22 Apr. 2011. That application is entitled "Head Set for Lingual Manipulation of an Object, and Method for Moving a Cursor on a Display," and issued on Nov. 12, 2013 as U.S. Pat. No. 8,579,766.

The CIP application was a continuation-in-part of U.S. Ser. No. 12/782,356, filed 18 May 2010. That application is entitled "Methods and Systems for Lingual Movement to Manipulate an Object," and issued Nov. 11, 2011 as U.S. Pat. No. 8,047,964 This non-provisional application, in turn, was a continuation-in-part of U.S. Ser. No. 12/556,237, filed 9 Sep. 2009, also entitled "Methods and Systems for Lingual Movement to Manipulate an Object." That application issued on May 17, 2011 as U.S. Pat. No. 7,942,782.

These related applications are each incorporated herein by reference in their entireties.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

BACKGROUND OF THE INVENTION

1. Field of the Invention

The present invention relates to dental devices. More specifically, the present invention relates to an intra-oral diagnostic tool for determining the existence of bruxing, or teeth grinding, during a patient's sleep.

2. Technology in the Field of the Invention

Many individuals experience grinding of their teeth. This most often occurs at night when the person is asleep and unaware of the occurrence. This event or condition is referred to medically as bruxism.

Some believe that bruxism is related to episodes of emotional stress. Bruxism can lead to a wearing of the tooth enamel. It can also lead to displacement of the internal temporomandibular structures. Further, excessive grinding can create headaches and jaw pain.

To prevent the damage resulting from grinding, dental professionals often prescribe a dental protector, commonly referred to as a night guard or a splint. The mouth guard acts as a protective barrier between the upper and lower sets of teeth, and is typically worn at night while the patient sleeps. The guard typically covers the upper set of teeth, thus separating both sets of teeth.

Oftentimes, dentists will make a mold of a patient's mouth in order to create a custom-fitted mouth guard. Such devices generally reduce the damage that bruxism can cause to teeth and supporting bone structure. However, such devices do not measure the degree of pressure being exerted by the patient at night, nor do they record when grinding is taking place or for how long. Further, the splints may not relieve the headaches induced by excessive grinding and clinching.

U.S. Pat. No. 6,089,864, issued in 2000, is entitled "Bio-Feedback, Data Acquisition Teeth Guards, Methods of their Manufacture and Use." This patent teaches a diagnostic device that fits within a patient's mouth. The device uses electrical sensors to detect the existence of pressure during grinding episodes. Upon detecting pressures greater than a designated threshold, a signal is sent. The signal activates bio-feedback referred to in the patent as a "human cognizable response." Such a response may include a sound, a vibration, an electrical stimulus, or other feedback delivered to the patient. The response is designed to awaken the patient so that grinding is stopped.

The mouth guard of the '864 patent is a complex device. In this respect, the mouth guard requires an integrated circuit, wires, and switches embedded in the mouth piece itself. Further, the device requires a transmitter and a biofeedback mechanism operating in real time.

Therefore, a need exists for an improved intra-oral apparatus that is inexpensive to manufacture, is disposable, and is light-weight. Further, a need exists for a mouth piece that relies upon pneumatic or fluid-based pressures within the patient's mouth rather than primarily on intra-oral electronics. Still further, a need exists for a diagnostic device that enables a health care professional to safely detect and/or monitor teeth grinding of a patient during the night, and that may be connected to a computer as part of cardio-respiratory (or other) monitoring, or even to an application on a portable device.

BRIEF SUMMARY OF THE INVENTION

First, an intra-oral system for monitoring bite pressures of a patient is provided herein. The system is beneficial for measuring or monitoring teeth clinching or grinding during sleep.

The system relies upon an elastomeric mouth piece. The mouth piece is dimensioned and configured to reside between the upper and lower teeth of a patient. The mouth piece has opposing left and right sides. The mouth piece further has an arcuate portion intermediate the left and right sides to form a generally horseshoe-shaped member.

The mouth piece has a plurality of cells embedded therein. The cells are configured to receive pressure applied by the teeth of the patient. At least one fluid-containing cell resides within the mouth piece on the left side, and at least one fluid-containing cell resides within the mouth piece on the right side. In one embodiment, two cells, or three cells, or even four separate cells, are provided on each of the left and the right sides of the mouth piece.

Each of the cells contains a fluid. The fluid may be air or some other non-toxic gas. In this instance, the cells may be referred to as air cells. Alternatively or in addition, the fluid may be water or other non-toxic liquid. In this case, the cells are fluid cells. For ease of reference, the cells will be described herein as simply that—cells.

The system also includes a plurality of tubes. Each tube has a proximal end and a distal end. The distal end of each of the tubes is in substantially sealed fluid communication with a corresponding cell. This may be by means of an integral connection between the distal end of the tubes and respective walls of the mouth piece. More preferably, the distal ends of the tubes are received in channels associated with the individual cells.

A plurality of transducers is also provided as part of the bite pressure monitoring system. Each transducer is in substantially sealed fluid communication with the proximal end of a corresponding tube. The transducers convert changes in pressure within the respective cells to corresponding electrical signals. Such electrical signals may be, for example, voltage signals, current signals, or resistive changes. The transducers are preferably in the nature of pressure sensors.

The system further includes a processor. The processor processes the electrical signals. The processor may include an analog-to-digital converter, meaning that electrical signals from the pressure sensors are converted into digital values. The converted electrical signals, such as voltage signals, are then modulated to generate a pressure profile from the cells. The pressure profile may represent a magnitude of pressure within each separate cell as a function of time.

In one aspect, the intra-oral system also includes an electronics box. The electronics box houses each transducer and the processor. The electronics box may include a VGA port for providing electrical communication with a computer monitor. Alternatively, the electronics box may include a transmitter for sending a wireless signal to a computer monitor so that a health care provider may observe teeth-grinding patterns in real time. Alternatively or in addition, the electronics box may include a USB or other data port for providing electrical communication with a separate computer. In this way, data collected from the patient during his or her sleep may be brought to a health care provider's office and uploaded for study.

A method for monitoring bite pressures of a patient during sleep is also provided herein. The method first includes providing an elastomeric mouth piece for a patient. The mouth piece is dimensioned to fit inside the mouth of a patient.

The mouth piece is designed in accordance with the mouth piece described above. In this respect, the mouth piece has opposing left and right sides, and an arcuate portion intermediate the left and right sides to form a generally horseshoe-shaped member. The mouth piece also has a plurality of cells embedded therein for receiving pressure applied by the teeth of the patient. At least one fluid-containing cell resides within the mouth piece on the left side, and at least one fluid-containing cell resides within the mouth piece on the right side. The fluid-containing cells are configured to respond to pressure applied by the upper and lower teeth of the patient.

The cells are in fluid communication with respective tubes. Each tube has a proximal end and a distal end. The distal end of each of the tubes is in substantially sealed fluid communication with a corresponding cell. The distal end of the tubes may be integral to the mouth piece; alternatively, the tubes are removable from the mouth piece or from channels associated with specific cells. In this latter instance, the method may include the step of placing a plurality of tubes in fluid communication with corresponding cells at a distal end of the tubes.

A proximal end of each of the tubes is in substantially sealed fluid communication with a corresponding transducer. The transducers convert changes in pressure within the respective cells to corresponding electrical signals. Such electrical signals may be, for example, voltage signals, current signals, or resistive changes. The transducers are preferably in the nature of pressure sensors.

The proximal end of the tubes may be integral to the transducers. Alternatively, the tubes are removable from the transducers, either directly or from a manifold connection. In this latter instance, each of the plurality of tubes comprises a jumper portion between a respective transducer and the manifold, and a mouth piece portion between the manifold and the mouth piece. The method may then include the step of placing the plurality of tubes in fluid communication with respective transducers.

The transducers are in electrical communication with a processor. The processor processes the electrical signals. The converted electrical signals, such as voltage signals, are then modulated to generate a pressure profile from the cells. The pressure profile is based upon pressure readings from the various cells. In one aspect, pressure signals are processed such that each electrical signal represents a pressure reading from a corresponding cell. Electrical signals from one or more corresponding cells may be averaged over a specified period of time to produce the pressure profile.

Preferably, the transducers and the processor reside within an electronics box external to the mouth piece. The electronics box may comprise a port for providing electrical communication with a computer monitor.

The method also includes placing the mouth piece into a patient's mouth between upper and lower teeth of the patient. The method then includes having the patient sleep for a period of time with the mouth piece in the patient's mouth. During this time, the tubes provide fluid communication between respective cells within the patient's mouth and corresponding transducers external to the mouth piece.

The method further includes reviewing a graph that shows bite pressure exerted by the patient as a function of time. The graph is reviewed by a dentist, a doctor, or other medical professional. Optionally, the graph is part of a cardio-respiratory monitoring system. Alternatively, the graph is viewed by the patient on his or her own portable electronic device, such as an iPad® or other tablet.

BRIEF DESCRIPTION OF THE DRAWINGS

So that the manner in which the present invention can be better understood, certain illustrations, charts and/or flow charts are appended hereto. It is to be noted, however, that the drawings illustrate only selected embodiments of the inventions and are therefore not to be considered limiting of scope, for the inventions may admit to other equally effective embodiments and applications.

FIGS. 2A through 2E show a mouth piece as may be used in the system of FIG. 1, in various views.

FIG. 2A is a perspective view of the mouth piece. Fluid tubes are removed in order to show openings for receiving the tubes.

FIG. 2B is another perspective view of the mouth piece from the system of FIG. 1. Here, the view is taken from behind a flange of the mouth piece.

FIG. 2C is a side view of the mouth piece from the system of FIG. 1.

FIG. 2D is a top view of the mouth piece from the system of FIG. 1.

FIG. 2E is a bottom view of the mouth piece from the system of FIG. 1.

In FIG. 5A, the electronics box is connected to the mouth piece via short fluid tubes. A cover of the electronics box has been removed to reveal electrical components.

In FIG. 5B, the electronics box is exploded away from the mouth piece. The cover has been placed over the electronics box.

FIG. 6 is a flowchart for a method for monitoring bite pressures of a patient during sleep, in one embodiment.

DETAILED DESCRIPTION OF CERTAIN EMBODIMENTS

Definitions

As used herein, the term "processor" means any computer-based processor having logic, such as a desk-top computer, a lap-top computer, or other general-purpose computer. In addition, the term "processor" includes a specially-dedicated system based on firmware or software. The processor may be a microprocessor, a microcontroller, a complex instruction set computing (CISC) microprocessor, a reduced instruction set (RISC) microprocessor, a very long instruction word (VLIW) microprocessor, or any other type of processor or processing circuit that may be embedded in an electrical circuit board for communicating with pressure transducers.

The term "computer" means any device having a processor and a display. For example, the term "computer" may be a desktop computer, a laptop computer, a tablet, or a so-called smart phone (e.g. iPhone, Android phone, Windows phone, etc.).

Description of Specific Embodiments

Figure 1:
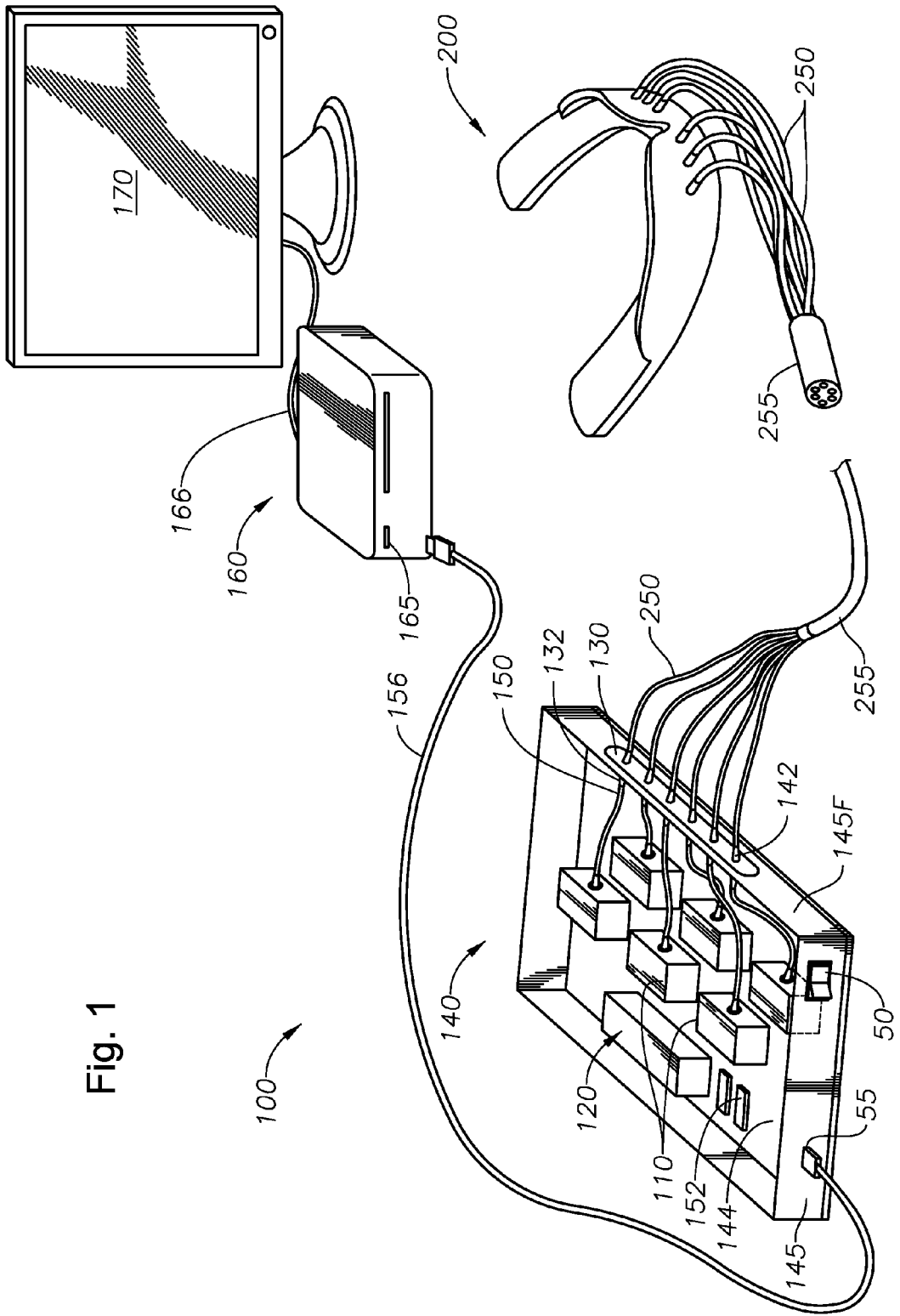
FIG. 1 is a perspective view of a bite pressure monitoring system according to the present invention, in one embodiment. A mouth piece is seen as part of the system, with the mouth piece having a plurality of tubes extending therefrom.

FIG. 1 is a perspective view of an intra-oral system 100 for monitoring bite pressure of a patient, in one embodiment. Various components of the system 100 are shown. The system 100 generally includes a mouth piece 200, a plurality of fluid-containing tubes 250 connected to the mouth piece 200, a plurality of transducers 110 in fluid communication with the fluid-containing tubes 250, and a processor 120. As will be described more fully below, the transducers 110 and the processor 120 reside within an electronics box 140.

The purpose of the pressure monitoring system 100 is to allow a doctor, a dentist, or other health care professional to monitor bite pressures of a patient. Preferably, this is done while the patient is sleeping. Monitoring of bite pressures may be done simultaneously with a number of other biological indices such as heart rate, breathing rhythm, blood pressure, and sleep patterns. Bite pressures are recorded as a function of time, and may then be displayed or printed out in graphical form.

The intra-oral pressure monitoring system 100 operates by means of the mouth piece 200. The mouth piece 200 is dimensioned and configured to be placed within a patient's mouth. The mouth piece 200 fits between the upper and lower teeth (not shown) of the patient.

The mouth piece 200 is preferably fabricated from an elastomeric material. Suitable materials may include polyisoprene rubber, chloroprene rubber, neoprene rubber, styrene butadiene rubber, and acrylonitrile butadiene rubber. Additional suitable examples include silicone, ethylene propylene diene methylene, polyvinylchloride, polyethylene, polyurethane, urethane-coated nylon, and ethyl vinyl acetate. Combinations of these materials may also be employed.

FIGS. 2A through 2E provide different views of the mouth piece 200 of FIG. 1. From these views, it can be seen that the mouth piece 200 has opposing left 210A and right 210B sides. The mouth piece 200 further has an arcuate portion 220 intermediate the left 210A and right 210B sides. The left side 210A, the right side 210B, and the arcuate portion 220 together form a generally horseshoe-shaped member 210.

FIG. 2A is a perspective view of the mouth piece 200. This view is generally taken from the front of the mouth piece 200. Six ports 225—three on each side of the mouth piece 200—are seen at the front of the mouth piece 200. These ports 225 are dimensioned to receive the fluid tubes 250. The tubes themselves are not shown in FIG. 2A, but are seen in FIG. 2E.

In FIG. 2A, it can be seen that the arcuate portion 220 has an extended height. In this way, the arcuate portion 220 forms an optional flange. The flange configuration helps to secure the mouth piece 200 in the patient's mouth during sleeping. The flanged arcuate portion 220 includes a vertical notch 222. The notch 222 accommodates the patient's connecting tissue that extends between the upper lip and gum. Additional notches (not shown) may optionally be added to accommodate a patient's canine teeth.

FIG. 2B is another perspective view of the mouth piece from the system of FIG. 1. Here, the view is taken from behind the flanged arcuate portion 220 of the mouth piece 200.

FIG. 2C is a side view of the mouth piece 200 from the system of FIG. 1. Here, the relative height of the flange configuration for the arcuate portion 220 relative to the horseshoe-shaped member 210 can be seen.

FIG. 2D is a top view of the mouth piece 200 from the system 100 of FIG. 1. The vertical notch 222 is noted in the center of the arcuate portion 220. In addition, a horizontal notch 212 is visible. The horizontal notch 212 allows the curvature of the horseshoe-shaped member 210 to comply with the shape of the patient's mouth. The horizontal notch 212 also allows the mouth piece 200 to more easily compress when inserting or removing the mouth piece 200 into a patient's mouth. Optionally, additional horizontal notches (not shown) may be employed.

FIG. 2E is a bottom view of the mouth piece 200 from the system 100 of FIG. 1. In this bottom view, left 210A and right 210B sides of the horseshoe-shaped member 210 are again seen. In addition, six illustrative tubes 250 are seen entering through the ports 225 and into the horseshoe-shaped member 210. The tubes 250 are shown in phantom.

The mouth piece 200, or at least portions of the left 210A and right 210B sides of the mouth piece 200, is designed to be substantially hollow. To this end, the mouth piece 200 includes a plurality of fluid-containing cells. In the arrangement of FIG. 2E, six cells are provided. These represent three cells 232A, 234A, 236A on the left side 210A, and three cells 232B, 234B, 236B on the right side 210B.

Cells 232A and 232B are "molar" cells. In this respect, cells 232A, 232B are positioned at the back of the mouth piece 200 and are designed to sense pressure between the upper and lower back molar teeth (not shown) of a patient. The back molars typically include the first and second molars. The back molars may also include wisdom teeth.

Cells 234A and 234B are "pre-molar" cells. As the name implies, cells 234A, 234B are positioned in the middle of the mouth piece 200 and are designed to sense pressure between the upper and lower pre-molar teeth (not shown) of a patient. Finally, cells 236A and 236B are "canine" cells. The canine cells 236A, 236B are positioned towards the front of the mouth piece 200 and are designed to sense pressure between the upper and lower canine teeth. Optionally, the canine cells 236A, 236B may extend forward towards the incisors of a patient.

Different numbers of cells may be used for a mouth piece 200. In one arrangement, only "molar" cells 232A, 232B are used. In another arrangement, only pre-molar cells 234A, 234B are used. In still another arrangement, only canine cells 236A, 236B are used. Still optionally, some combination of these cells is provided.

It is also noted that the cells may be re-configured to target individual teeth. For example, the molar cells 232A, 232B may be divided into separate cells to separately sense pressure between the wisdom teeth, or between specific molars. Alternatively, the pre-molar cells 234A, 234B may be divided into separate cells to separately sense pressure between specific pre-molar teeth. In these instances, the mouth piece 200 may need to be custom-designed to match the patient's specific dental anatomy.

Each cell 232A, 234A, 236A, 232A, 234B, 236C holds a volume of fluid. The fluid may be a compressible fluid, or gas. The compressible fluid may be air or another non-toxic gas. The compressible fluid may comprise oxygen, carbon dioxide, nitrogen, argon, helium, or combinations thereof. Alternatively, the fluid may be a substantially non-compressible fluid, such as water or other non-toxic liquid. A combination of compressible and non-compressible fluids may also be employed. In any instance, fabrication of the intra-oral system 100 will typically involve establishing a baseline pressure within the cells 232A, 234A, 236A, 232B, 234B, 236B.

Preferably, the fluid is held at ambient pressure. Alternatively, the fluid in the cells 232A, 234A, 236A, 232B, 234B, 236B is pre-loaded at a higher pressure such as between about 15 psi and 30 psi. In this way, the mouth piece 200 is at least nominally resistive to pressure placed by the patient using his or her teeth. The tubes 250 may include one-way valves (not shown) that allow a user to insert fluid into the tubes 250 once the tubes 250 are in place.

To define the cells 232A, 234A, 236A, 232B, 234B, 236B, the mouth piece 200 includes a series of walls 238. The walls 238 are sealed between bottom and top surfaces (not numbered) along the horseshoe-shaped member 210. Sealing may be through heat sealing, RF sealing, or other mechanisms known in the art of plastic injection molding or other molding techniques.

The cells 232A, 234A, 236A, 232B, 234B, 236B of the mouth piece 200 are in fluid communication with respective tubes 250. The tubes 250 are again seen in the bottom view of FIG. 2E. Each cell 232A, 234A, 236A, 232B, 234B, 236B receives its own tube 250. The tubes 250 are sealingly disposed within the walls 238 of the mouth piece 200. The tubes 250 are preferably manufactured to be integral to respective walls 238 and the ports 225.

The mouth piece 200 and the connection to the tubes 250 may be configured in different sizes. The size will primarily be dictated by the size of the individual user's mouth. It is noted that for smaller users, fewer cells may be necessitated due to size limitations. The number of cells will also affect the manner in which the system 100 is programmed.

In the mouth piece 200 of FIGS. 2A through 2E, the tubes 250 connect to the walls 238 internal to the mouth piece 200. However, some or all of the tubes 250 may alternatively enter the cells 232A, 234A, 236A, 232B, 234B, 236B from a top, a bottom or an outer edge of the mouth piece 200. The present inventions are not limited by the method of providing fluid communication between the tubes 250 and the cells unless so provided in the claims.

Referring back to FIG. 1, the tubes 250 are optionally bundled as they exit the mouth piece 200. This means that the tubes 250 are held together externally by a tubular sheath 255. The tubular sheath 255 protects the individual tubes 250, and also prevents them from becoming tangled and constricted.

The mouth piece and tubes arrangement of FIGS. 2A through 2E is merely illustrative. Other arrangements for the mouth piece 200 and tubes 250 may be provided. One alternate arrangement is shown in FIGS. 3A and 3B.

Figure 3A:
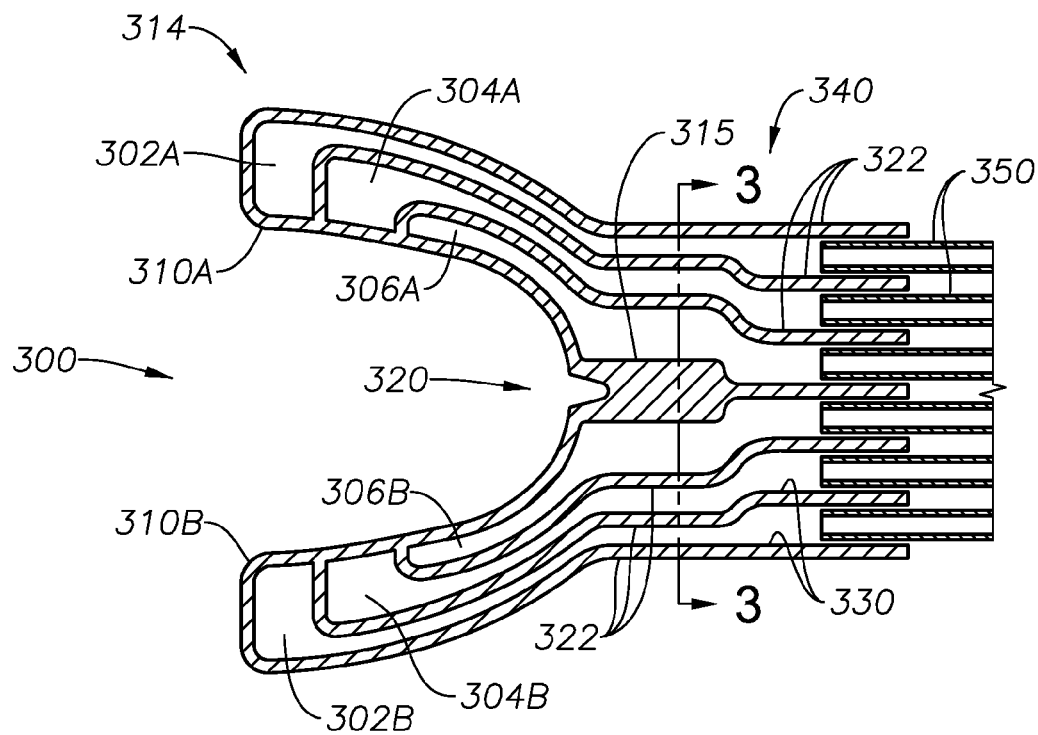
FIG. 3A is a top, cross-sectional view of a mouth piece as may be used with a bite pressure monitoring system of the present inventions, in an alternate embodiment.
Figure 3B:
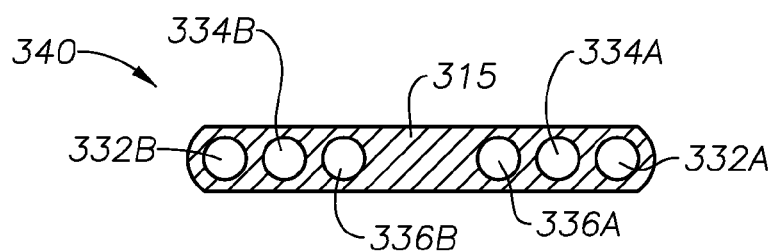
FIG. 3B is a cross-sectional view of the mouth piece of FIG. 3A, taken across line 3-3.

FIG. 3A is a top, cross-sectional view of a mouth piece 300 as may be used in the intra-oral system 100 of FIG. 1, in an alternate embodiment. FIG. 3B is a cross-sectional view of the mouth piece 310 of FIG. 3A, taken across line 3-3. The mouth piece 300 provides an arrangement wherein integral channels communicate fluid pressure between individual cells and corresponding tubes 350. The mouth piece 300 will be described with reference to FIGS. 3A and 3B, together.

The mouth piece 300 has opposing left 310A and right 310B sides. Both the left 310A and the right 310B sides include at least one, and preferably at least three, fluid-containing cells. In the arrangement of FIG. 3A, three cells are provided on each side. These are cells 302A, 304A, 306A on the left side 310A, and cells 302B, 304B, 306B on the right side 310B.

Cells 302A and 302B are "molar" cells. In this respect, cells 302A, 302B are positioned at the back of the mouth piece 300 and are designed to sense pressure between the upper and lower back molar teeth of a patient. If the patient has wisdom teeth, the cells 302A, 302B will reside between the wisdom teeth as well.

Cells 304A and 304B are "pre-molar" cells. As the name implies, cells 304A, 304B are positioned in the middle of the mouth piece 300 and are designed to sense pressure between the upper and lower pre-molar teeth of a patient. Finally, cells 306A and 306B are "canine" cells. The canine cells 306A, 306B are positioned towards the front of the mouth piece 300 and are designed to sense pressure between the upper and lower canine teeth. Cells 306A, 306B may also be configured to sense pressure between upper and lower incisors.

As with mouth piece 200, different numbers of cells may be used for the mouth piece 300. In one arrangement, only "molar" cells 302A, 302B are used. In another arrangement, only pre-molar cells 304A, 304B are used. In still another arrangement, only canine cells 306A, 306B are used. Still optionally, some combination of these cells is provided.

The mouth piece 300 also has an arcuate portion 320. The arcuate portion 320 resides intermediate the left 310A and right 310B sides. Extending from the arcuate portion 320 is an elongated central wall 315. In addition, a plurality of outer walls 322 extends from the arcuate portion 320 generally parallel to the central wall 315.

The central wall 315 and the various outer walls 322 form a series of substantially parallel channels. The walls 315, 322 and the channels reside in a transition section 340 of the mouth piece 300. The channels within the transition section 340 are in fluid communication with respective cells.

In FIG. 3A, the channels are not numbered; however, in FIG. 3B the channels are numbered as 332A, 334A, 336A on one side, and 332B, 334B, 336B on the other side. The channels correspond to specific cells as follows:

channel 332A corresponds to cell 302A;
channel 334A corresponds to cell 304A;
channel 336A corresponds to cell 306A;
channel 332B corresponds to cell 302B;
channel 334B corresponds to cell 304B;
channel 336B corresponds to cell 306B;

Each cell 302A, 304A, 306A, 302B, 304B, 306B and its corresponding channel 332A, 334A, 336A, 332B, 334B, 336B forms a volume for holding fluid. The cells and corresponding channels preferably have substantially similar volumes. However, this is not critical, as the cells and corresponding channels may be pre-loaded with fluid so as to equalize pressures among the cells.

Each channel 332A, 334A, 336A, 332B, 334B, 336B is configured to sealingly receive a respective tube 350 The channels 332A, 334A, 336A, 332B, 334B, 336B place the cells 302A, 304A, 306A, 302B, 304B, 306B in fluid communication with respective tubes 350. The tubes 350, in turn, transmit pressure to respective transducers, which in turn convert pressure values into electrical signals.

Figure 4:
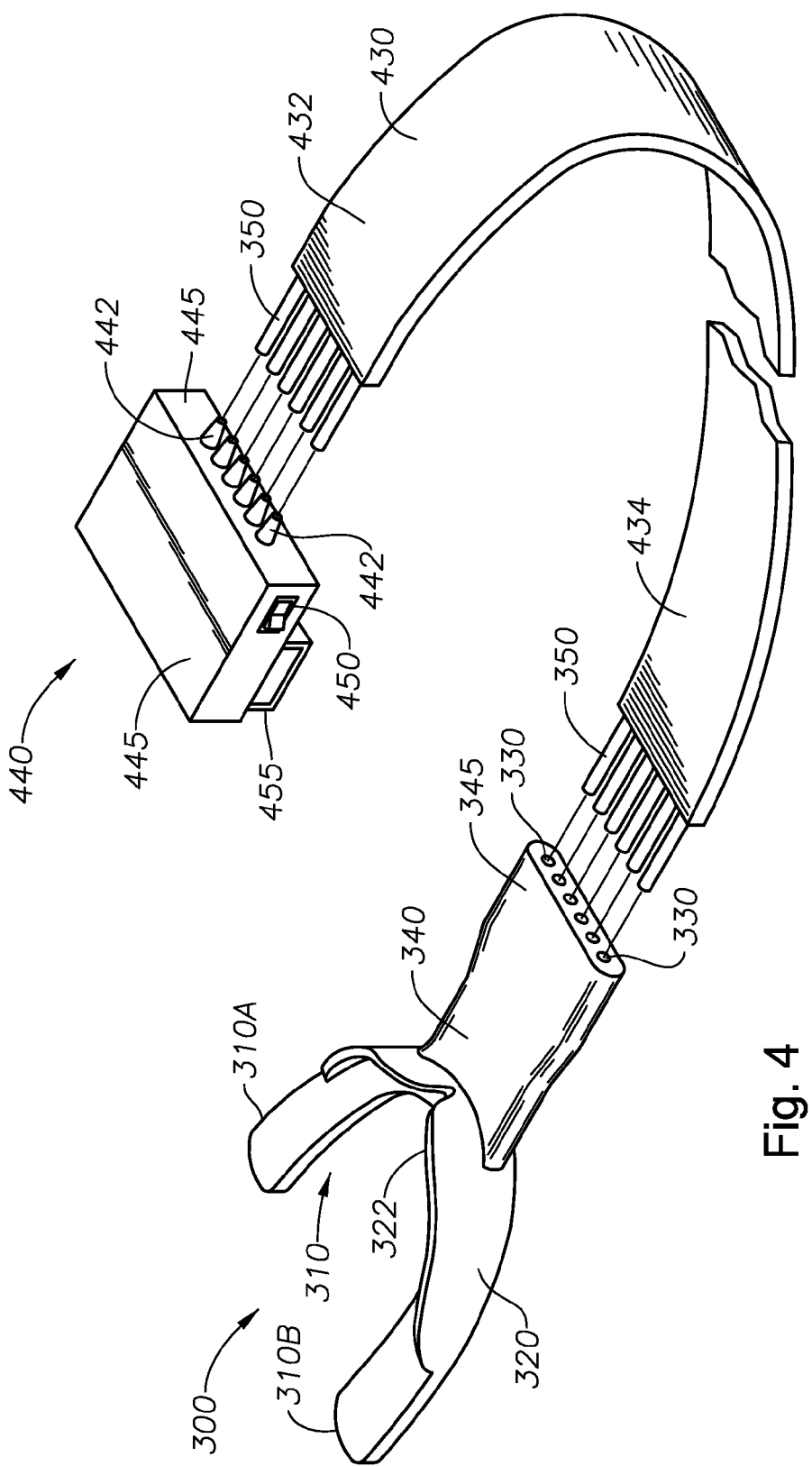
FIG. 4 is a perspective view of the mouth piece of FIG. 3A, along with a tube bundle. Here, the tube bundle is in the nature of a ribbon cable. The tube bundle is exploded away from the mouth piece at one end, and from an electronics box at an opposite end.

The tubes 350 are preferably carried from the mouth piece 300 to the transducers in a tube bundle. FIG. 4 provides a perspective view of an illustrative tube bundle 430 provided between a mouth piece and electronics. In FIG. 4, the mouth piece 300 of FIG. 3 is shown. The transition section 340 is seen extending from the mouth piece 300 and to the tube bundle 430. In the arrangement of FIG. 4, the transition section 340 has a widened end 345 to make it easier for a user to insert the tubes 350 into channels 330.

The tube bundle 430 is in the form of a ribbon cable. The tube bundle 430 has a proximal end 432 and a distal end 434. The proximal end 432 connects to an electronics box 440, while the distal end 434 connects to the transition section 340 of the mouth piece 300. The connections may be made through a simple friction fit.

The tube bundle 430 houses the plurality of tubes 350. In the arrangement of FIG. 4, the tubes 350 extend from both the proximal end 432 and the distal end 434. At the proximal end 432, the tubes 350 slide either into or over nozzles 442 that extend from the electronics box 440. At the distal end 434, the tubes 350 are received into the channels 330. Channels 330 are representative of the individual channels 332A, 334A, 336A, 332B, 334B, 336B of FIG. 3B.

The electronics box 440 is configured to house electronics for operating the bite pressure monitoring system 100. The electronics may include transducers, a processor, a battery, and an integrated circuit board. Preferably, the processor will be consolidated with memory and an analog-to-digital converter in one chip. The electronics box 440 may also include short jumper tubes that place the tubes 350 of the tube bundle 430 in fluid communication with the transducers via the nozzles 442. These various components are not visible in FIG. 4, as the electronics box 440 is shown in a closed state. Walls 445 are seen forming the electronics box 440.

FIG. 4 does show a power switch 450 associated with the electronics box 440. The power switch 450 enables the health care provider to conserve battery power when the electronics box 440 is not being used. Of course, it is understood that the electronics box 440 may alternatively be powered by a power cable (not shown) that may be plugged into an outlet.

The electronics box 440 also includes a data port 455. The data port 455 may be a USB port for connecting the electronics box 440 with a general purpose computer using a cable. The data port 455 may alternatively be a transmitter that transmits signals from the processor to a general purpose computer. In this instance, the transmission is wireless, and communicates with a second processor using an RF signal, or by using other wireless means such as Bluetooth, IR, Wi-Fi, or Wi-Max.

The tube bundle 430 arrangement of FIG. 4 is ideal as it allows tubes 350 to be selectively connected and disconnected to the mouth piece 300 and the electronics box 440. This facilitates periodic cleaning of the tubes 350 and the ability of each patient to save his or her own tube bundle 430 when the mouth piece 300 is replaced. Of course, it is understood that the tube bundle 430 may alternatively be designed to be integral to the mouth piece 300, the electronics box 440, or both.

Returning to FIG. 1 now, FIG. 1 shows an electronics box 140 for housing electrical components of the intra-oral monitoring system 100. The electronics box 140 is designed in the same manner as the electronics box 440 of FIG. 4. However, in FIG. 1 a top wall of the box 140 has been removed, revealing various components.

The electronics box 140 is framed by side walls 145. A front wall 145$f$ of the electronics box 140 includes a manifold 130. The manifold 130 includes an array of nozzles 142 extending outwardly from the front wall 145$f$. The nozzles 142 receive respective tubes 250. The tubes 250 may be referred to as mouth piece tubes as they extend from the mouth piece 200. Preferably, the tubes 250 are bundled in the tubing sheath 255. The sheath 255 protects the tubes 250 and keeps them from becoming tangled.

A separate grouping of nozzles 132 is located on the internal side of the manifold 130. These nozzles 132 receive short jumper tubes 150 at one end. At an opposite end, the jumper tubes 150 are connected to respective transducers 110. The jumper tubes 150 place the transducers 110 in fluid communication with the air tubes 150 and the individual cells of the mouth piece 200 via the manifold 130.

The transducers 110 are in the nature of pressure sensors. The transducers 110 may be, for example, ASDX pressure sensors made by the Sensing and Control Division of Honeywell in Golden Valley, Minn. The ASDX series of pressure sensors utilize a small internal diaphragm for sensing fine variations in pressure. Different sensors are offered in the series for sensing within different pressure ranges. Such ranges include 0 to 1 psi, 0 to 5 psi, 0 to 15 psi, and 0 to 30 psi. The ASDX sensors offer a high level output (5.0 Vdc span) that is fully calibrated and temperature compensated with on-board Application Specific Integrated Circuitry (ASIC).

The manifold 130 includes fluid channels (not shown) between the respective nozzles 142, 132. In this way the jumper tubes 150 are in fluid communication with the mouth piece tubes 250. Use of the manifold 130 also enables the health care professional to achieve fluid communication between the mouth piece 200 and the transducers 110 without necessity of the operator opening the electronics box 140 and exposing the delicate transducers 110 and the processor (or micro-controller) 120. Further, the health care professional is not required to manipulate the fragile connections between the jumper tubes 145 and the respective transducers 110.

Preferably, the jumper tubes 150 and the mouth piece tubes 250 are color-coded with the array of nozzles 142/132 so that the tubes 250 properly correspond to the correct transducers 110. Alternatively, other coding systems may be used such as alphabetical or numeric associations, or the use of symbols. Alternatively still, custom connectors which connect the tubes 250 to the nozzles 142 in only one orientation may be utilized.

As noted, the electronics box 140 also includes a processor 120. Preferably, the processor 120 is a micro-controller. The micro-controller 120 may be, for example, an Atmel® AVR® 8-bit microcontroller, useful for C and assembly programming. As another example, the micro-controller 120 may be the Atmel® 8-bit AVR RISC-based micro-controller that combines 16 KB ISP flash memory, 1 KB SRAM, 512B EEPROM, and an 8-channel/10-bit A/D converter (TQFP and QFN/MLF). The device supports a throughput of 20 MIPS at 20 MHz and operates at between 2.7 and 5.5 volts.

A power switch 50 is also provided on the electronics box 140. The power switch 50 is associated with the electronics, such as the transducers 110 and the processor 120. It is understood that the electronics will also include an analog-to-digital converter ("ADC") for converting analog signals from the transducers 110 into digital signals for the processor 120. The ADC converter may be integral to the transducers 110, or may be separate.

The electronics box 140 may optionally also include batteries 152. The power switch 50 switches power from the batteries 152 to the electronics on and off. Where batteries 152 are not used, an electrical cord (not shown) may extend from the electronics box 140. The cord may connect to a power pack (not shown), that may then plug into an electrical outlet for power.

Within the walls 145 of the electronics box 140, at a base of the box 140, is a printed circuit board 144. The printed circuit board 144 or integrated circuit provides electrical connectivity between the transducers 110 and the processor 120. Other common circuit features may be associated with the circuit board 144 such as a clock or timer, resistors, capacitors, and the like as may be used in surface mounting.

It is noted that the use of a manifold 130 is optional. In one aspect, the tubes 250 connect directly from the mouth piece 200 to the transducers 110 at a proximal end. Even when the manifold 130 is used, the jumper tubes 150 and mouth piece tubes 250 together form common tubes such that a proximal end of the tubes 150/250 is connected to the transducers 110, while a distal end of the tubes 150/250 is connected to the mouth piece 200 (or 300).

In operation, the patient is supplied with his or her own mouth piece, such as mouth piece 300. The tubes 350 associated with the mouth piece may be integral to the mouth piece, or may be separate. Further, tubes may be pre-connected to or be integral to the manifold 130 at the proximal end, or may be separate. Preferably, the tubular bundle 430 is used, with the health care professional connecting the tubes 350 at the proximal end 432 of the tubular bundle 430 to the manifold nozzles 442, and the tubes 350 at the distal end 434 of the tubular bundle 430 to the channels 330 of the mouth piece 300. In this way, the tube bundle 430 is sold separately, and may be easily replaced in the event of rupture or other damage.

As noted, it may also be desirable to pre-load the cells and associated tubes 350 with a small amount of air pressure or fluid pressure. This may be done "in the field" by providing one-way valves (not shown) in the tubes 350 or in the manifold 130 that are associated with each of the tubes 350. The valve enables the operator to calibrate the transducers 110, and establishes a more accurate conversion of pressure changes to electrical signals by the transducers 110. A small air or fluid pump may then be used to inject air or water through the valves (not shown) into the tubes.

After making the connection between the tubes 350 and the manifold 130, and after pre-loading the cells, the power switch 50 to the electronics box 140 is turned on. The electronics box 140 is supported on or near the patient's bed. For example, the electronics box 150 may be mounted on a bed frame or placed on a stand next to the bed. The health care professional then assists the patient in properly placing the mouth piece 200 (or 300) in his or her mouth, between the lower and upper teeth. The patient then goes to sleep.

During a period of sleep, the patient may begin to grind his or her teeth. This causes changes in pressure within the cells of the mouth piece 200. The transducers 110 sense the changes in pressure within the cells and convert them to electrical signals. The electrical signals may be analog voltage signals. Other examples of electrical signals that may be used include current signals or resistive changes. The changes in pressure within the cells are delivered pneumatically or fluidically, depending on the fluid used, to the transducers 110 through the respective tubes 250 (or 350). As the transducers 110 sense an increase in pressure, a corresponding voltage or other electrical signal is delivered through the electrical circuit board 144 to the processor 120, such as a micro-controller.

The processor 120 uses operational software for processing the electrical signals. The electrical signals are delivered to the processor 120 by means of the electrical circuit board 144. The electrical signals, such as voltage signals, are then interpreted to generate a pressure profile from the cells, such as cells 302A, 304A, 306A, 302B, 304B, 306B. The pressure profile represents a magnitude of pressure from within the cells as a function of time.

The pressure profile is based upon pressure readings from the various cells, either individually or through some combination. In one aspect, pressure signals are processed such that each electrical signal represents a pressure reading from a corresponding cell. The pressure profile may, thus, represent a separate line for each cell on a graphical display. Electrical signals from each cell may be read instantaneously, or the various signals from each cell may be averaged over a specified period of time to produce the pressure profile. A baseline or steady-state value representing no pressure being applied to the mouth piece 110 may be subtracted from the pressure profile to more accurately determine the actual pressure applied by the patient.

In one aspect, a chip having processing capabilities is used to average pressure readings from all cells. Alternatively, a combined or total value of all pressure readings from all cells is generated. In either aspect, a single value, rather than separate values for each cell, may optionally be provided, showing pressure as a function of time.

When a pressure profile is generated, a normalization procedure may be used to remove differences in pressure-to-voltage characteristics between cells. These differences can arise due to manufacturing imperfections in the cells and/or the electronics. Differences can also arise due to incidental variations in fluid volume within the cells, or incidental differences in volume size between the cells and associated tubes 350. The normalization values can be stored on the processor 120.

Referring again to FIG. 1, the electronics box 140 has a data port 55. The data port 55 may be a wireless transmitter that transmits signals from the processor 120 to a general purpose computer, shown at 160. In this instance, the processor 120 communicates with the computer 160 using an RF signal, or by using other wireless means such as Bluetooth, IR, Wi-Fi, or Wi-Max. More preferably, the data port 55 is a USB port for connecting the electronics box 150 with the general purpose computer 160 using a cable 156. The computer 160 has a VGA cable 166 that connects to a monitor 170.

After the patient has slept for a period of time, the USB cable 156 may be connected to the computer 160. A USB port 165 is provided on the computer 160 for making an electrical connection. Software associated with the computer 160 then enables a health care professional to view and print out a graphical representation of the pressure profile. In this way, the health care professional may determine whether, and to what extent, bruxism is taking place. Further, where a separate profile is generated for each cell, the health care professional may identify areas of the mouth where the greatest degree of bruxism is occurring.

Figure 5A:
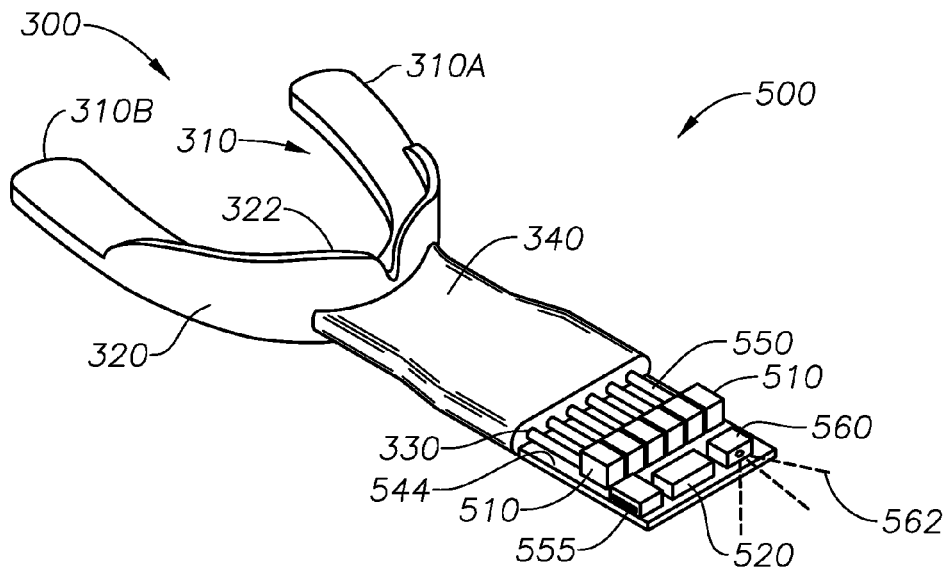
FIGS. 5A and 5B present perspective views of the mouth-piece of FIG. 3A. Here, the mouth piece receives an electronics box that fits onto the mouth piece.
Figure 5B:
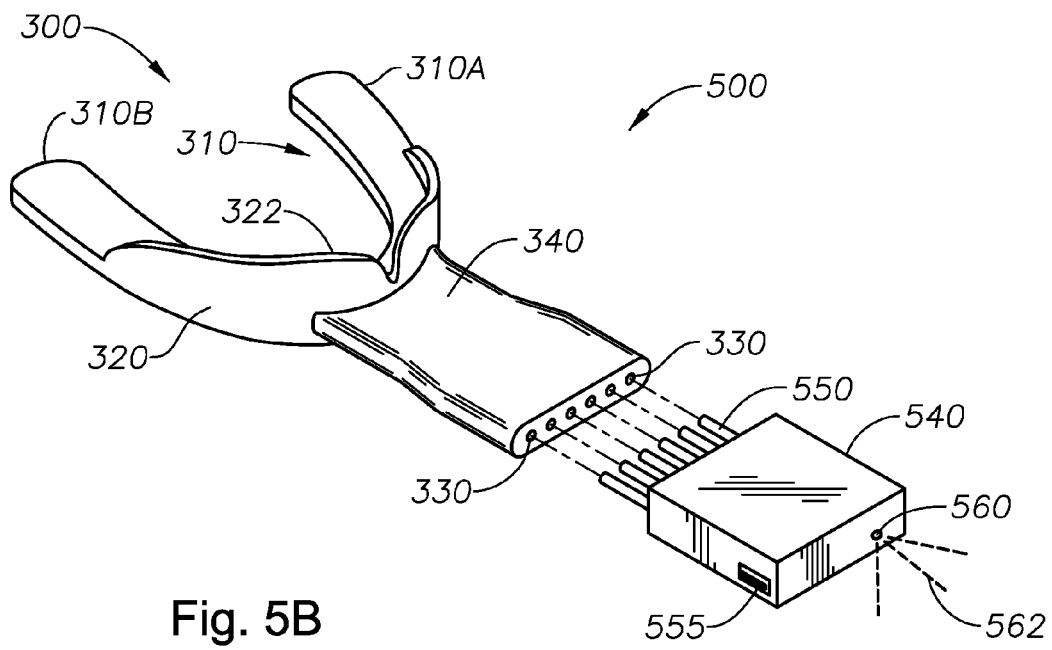

FIGS. 5A and 5B present perspective views of the mouth piece 300 of FIG. 3A. Here, the mouth piece 300 receives an electronics box 540 that fits immediately onto the transition section 340 of the mouth piece 300. Therefore, a modified bite pressure monitoring system 500 is provided.

In FIG. 5A, the electronics box 540 is connected to the mouth piece 300 via short fluid tubes 550. Additional mechanical support (not shown) may optionally be provided for securely holding the electronics box 540 onto the mouth piece 300. Preferably though, the transition section 340 of the mouth piece 300 and the short fluid tubes 550 are fabricated from a rigid thermoplastic material that enables the mouth piece 300 and tubes 550 together to support the electronics box 540. The short, non-bundled fluid tubes 550 are in lieu of the longer "ribbon cable" 430 used for bundling the fluid tubes 350 in the embodiment of FIG. 4.

In FIG. 5B, the electronics box 540 is exploded away from the mouth piece 300. The fluid tubes 550 are seen extending away from the electronics box 540. A distal end of each of the tubes 550 is configured to be received in corresponding channels 330 of the transition section 340. Ideally, the rigid fluid tubes 550 will extend at least half an inch to an inch into the channels 330 to provide the needed mechanical support for the electronics box 540.

In FIG. 5A, various electrical components are seen associated with the electronics box 540. These include transducers 510, a processor 520, and an electrical circuit board 544. The transducers 510 operate in accordance with transducers 110 shown in FIG. 1 and described above. Similarly, the processor 520 operates in accordance with processor 120 of FIG. 1 described above. In this respect, the processor 520 uses operational software for processing electrical signals from the transducers 510. The electrical signals are delivered to the processor 520 by means of the circuit board 544. The electrical signals, such as voltage signals, are then interpreted to generate a pressure profile from the cells, such as cells 302A, 304A, 306A, 302B, 304B, 306B from FIG. 3A. The pressure profile represents a magnitude of pressure from within the cells as a function of time. The pressure profile may show each cell separately, or may combine or average the pressures of the cells in some way.

The processor 520 stores the pressure profile in memory. The pressure profile may be uploaded to a separate computer using a data port 555. In FIG. 5B, the data port 555 is shown as a USB connection. However, it is understood that other types of data ports may be developed and used, presently or in the future.

As an additional feature, the bite pressure monitoring system 500 of FIG. 5A optionally also includes a transmitter 560. The transmitter 560 transmits wireless signals 562. The signals 562 are indicative of the pressure profile generated by the processor 520. The signals 562 are transmitted to a transceiver (not shown) associated with a monitor. In this way, a health care professional may watch the patient's teeth-grinding pattern in real time. This is preferably done along with cardio-respiratory monitoring.

The signals 562 may be transmitted as radio-frequency (RF) or infrared (IR) signals. Alternatively, the signals 562 may be other wireless means such as Bluetooth, Wi-Fi, or Wi-Max.

In another aspect, the transceiver stores the pressure profile into a digital file on a computer. The computer may be a portable, hand-held electronic device such as a so-called smart phone, or may be a so-called tablet computer. The hand-held device will include a program or "app" that may be accessed for later viewing by the patient or by a health care provider.

Other components may be used with the electronics box 540 and the electrical circuit board 144. These may include a battery, a clock or timer, resistors, capacitors, and the like. A cover 541 is also preferably provided for the electronics box 540. In FIG. 5A, the cover has been removed to reveal selected electrical components therein. However, in FIG. 5B the cover 541 has been placed over the electronics box 540 to protect the delicate electrical devices inside therein.

Based on the various embodiments of bite pressure monitoring systems described above, a method 600 for monitoring bite pressures of a patient during sleep is also provided herein. FIG. 5 presents a flow chart, showing steps for generally performing the method 600, in one embodiment.

The method 600 first includes providing an elastomeric mouth piece for a patient. This is shown at Box 610 of FIG. 5. The mouth piece is dimensioned to fit inside the mouth of a patient.

The mouth piece is generally designed in accordance with the mouth pieces 200 or 300 described above, in their various embodiments. In this respect, the mouth piece has opposing left and right sides, and an arcuate portion intermediate the left and right sides to form a generally horseshoe-shaped member.

The mouth piece also has a plurality of fluid-containing cells embedded therein for receiving pressure applied by the teeth of the patient. The cells are divided and sealed by walls. At least one fluid-containing cell resides within the mouth piece on the left side, and at least one fluid-containing cell resides within the mouth piece on the right side. The fluid-containing cells are configured to respond to pressure applied by the upper and lower teeth of the patient.

The fluid in the fluid-containing cells may be a compressible fluid, or gas. The compressible fluid may be air or another non-toxic gas. Alternatively, the fluid may be a substantially non-compressible fluid, such as water or other non-toxic liquid. A combination of compressible and non-compressible fluids may also be employed. In any aspect, the fluid-containing cells are embedded into the mouth piece for receiving pressure applied by the teeth of an individual.

The mouth piece is designed to interact with a plurality of tubes. Each tube has a proximal end and a distal end. The distal end of each of the tubes is in substantially sealed fluid communication with a corresponding cell. Preferably, the tubes are received in respective channels external to the mouth piece that are part of a transition section. In this way, the tubes may be retained, sterilized, and re-used when the mouth piece is disposed of.

In one embodiment, the method 600 includes the step of placing the plurality of tubes in fluid communication with corresponding cells. This is shown in Box 620. Ideally, the cells are connected to fluid channels (such as channels 330) which may then receive tubes (such as tubes 350). The tubes and corresponding fluid channels may be color coded so that the health care provider and patient may know how to make the connection. However, in some instances the tubes may be pre-connected to the mouth piece so that this step is not needed by a health care provider.

Each tube has a proximal end and a distal end. The distal end of each of the tubes is placed in substantially sealed fluid communication with a corresponding cell of the mouth piece. In one aspect, each of the tubes comprises more than one tubular body operatively connected to form a single, pneumatically-sealed channel. In this instance, a manifold may be used to provide a "quick-connect" between sets of tubes. The manifold is preferably part of an electronics box. In another embodiment, the tubes are short, rigid tubes.

Preferably, each of the plurality of tubes is an air tube that resides substantially at ambient pressure. Alternatively, each of the plurality of tubes may be preloaded at a pressure of about 15 psi to 30 psi. This creates desirable additional resistance for patients. Preloading the tubes and cells also provides flexibility for the operator in calibrating or "tuning" the system so that pressure readings are accurate. The tubes preferably have an inner diameter of about 0.05 inches to 0.5 inches. However, other dimensions may be employed.

It is preferred that the tubes be used at a standard temperature, such as 72° F. Those of ordinary skill in the art will understand that air or fluid pressure within the tubes may be affected by the temperature in the operating environment.

The method 600 may further include the step of placing each of the plurality of tubes in fluid communication with a corresponding transducer. This is provided in Box 630. More specifically, the proximal end of each tube is in fluid communication with a transducer.

Preferably, the transducers and the processor reside within an electronics box external to the mouth piece. The electronics box may comprise a port for providing electrical communication with a computer monitor, and a manifold having a number of nozzles. In this instance, each of the plurality of tubes may comprise a jumper portion between a respective transducer and the manifold, and a mouth piece portion between the manifold and the mouth piece. The jumper portion of the tubes and the mouth piece portion of the tubes are each connected through the nozzles of the manifold to form a single set of tubes.

The tubes may come pre-connected to the electronics box. Alternatively, the healthcare provider or patient may make the connection. In this latter instance, the step of Box 530 may comprise placing the mouth piece portion of each of the plurality of tubes into fluid communication with a transducer through the manifold. In one embodiment, the fluid tubes are short, rigid tubes that allow the electronics box to be connected immediately to a transition section of the mouth piece. Each tube slidably and frictionally extends into a corresponding channel in the transition section.

Regardless of the tubing arrangement, each transducer is preferably a pressure sensor having a diaphragm that is sensitive to changes in pressure within a corresponding tube. The transducers convert changes in pressure within the cells to voltage or other electrical signals. The electrical signals are sent to a processor. The processor receives the voltage (or other electrical) signals from the transducers and processes them.

The method 600 also includes the step of having a patient sleep for a period of time with the mouth piece in the patient's mouth. This is seen at Box 640. The mouth piece may be inserted into the patient's mouth by either a health care professional or by the patient himself (or herself). A health care professional may determine the desired length of time to obtain an accurate profile of bite pressures.

As the patient sleeps, he or she may begin to grind their teeth. The mouth piece helps to prevent wearing of the tooth enamel. The mouth piece may further help to reduce the effects of stress-related grinding, such as temporal mandibular joint syndrome and headaches. More importantly, the mouth piece, through the fluid-containing cells and the processor, creates a pressure profile.

The pressure profile is generated by the processor in response to the voltage or other electrical signals received from the transducers. The pressure profile is based upon pressure readings from the various cells. In one aspect, pressure signals are processed such that each voltage signal represents a pressure reading from a corresponding cell. Alternatively, electrical signals from one or more corresponding transducers may be averaged over a specified period of time, or may be totaled at intervals, to produce the pressure profile. In any arrangement, the signals are modulated by the processor to generate a pressure profile from the cells as a function of time.

The method 600 further includes reviewing a graph that shows bite pressure exerted by the patient as a function of time. This is provided at Box 650. The graph is reviewed by a dentist, a doctor, or other medical professional. The health care professional may compare the pressure profile to a baseline to determine if pressure readings exceed the baseline. This may be helpful as a diagnostic tool in, for example, determining whether bruxism is the source of the patient's symptoms. Alternatively, the health care professional may determine where along the dental structure that bruxism is taking place, and at what time periods of the night.

It is noted that for most patients, bite force will vary in different regions of the oral cavity. The more posteriorly the fluid cells are located along the dental arch, the greater the bite force measurements will be. Thus, the baseline for bite force can vary depending on location along the dental arch.

In addition, the baseline, or "norm," will vary depending on different factors. These may include age, gender, and the presence vel non of masticatory muscle pain and/or temporomandibular joint (TMJ) inflammation in the patient. Overall, a healthcare provider may be concerned about any nocturnal bite pressure readings that exceed, for example, an average of 25 N or greater over a 10 minute period, or, alternatively, an average of 50 N or greater, or 200 N or greater, over a 5 minute period. In one aspect, the processor compares average pressure readings from the fluid cells to a designated baseline for the patient.

As can be seen, a unique mouth guard is offered that allows a health care professional to monitor bite pressures of a patient during sleep or other period of time. The graph that is reviewed in the step of Box 650 may be reviewed on a computer monitor, such as the monitor 170 shown in FIG. 1. Alternatively, the graph may be printed out and reviewed and interpreted. Optionally, the graph is part of a cardio-respiratory monitoring system. In this instance, the graph may also include such bio-indices as heart rate, oxygen saturation, breathing rhythm, and sleep patterns.

In one aspect, reviewing the graph of Box 650 comprises monitoring bite pressures of a patient in real time, using a monitor that is in a room separate from the patient. In another aspect, the graph is saved as a digital file on a computer or on a network, and is reviewed by a health care professional at a later date. In another instance, the pressure profile of a patient may be uploaded from the electronics box to a computer residing in a health care provider's office. The pressure profile may be synched with other time-based medical data such as pH of gastric fluids, breathing rhythm, and heart rate.

While it will be apparent that the inventions herein described are well calculated to achieve the benefits and advantages set forth above, it will be appreciated that the inventions are susceptible to modification, variation and change without departing from the spirit thereof. For example, it is within the scope of the present disclosure to have a complete system, that is, a mouth guard, associated tubes, and a processor within an electronics box offered as a package. A patient may purchase the system, use the system, and have the teeth-pressure results wirelessly transmitted to his or her own handheld computer. An application is provided on the handheld device for viewing the pressure data after using the system while asleep.

I claim:

1. An intra-oral system for monitoring bite pressures of a patient during sleep, the system comprising:
    an elastomeric mouth piece dimensioned and configured to reside between the upper and lower teeth of a patient, the mouth piece comprising opposing left and right sides, and an arcuate portion intermediate the left and right sides to form a horseshoe-shaped member;
    at least one fluid-containing cell residing within the mouth piece on the left side, and at least one fluid-containing cell residing within the mouth piece on the right side, the fluid-containing cells being configured to respond to pressure applied by the teeth of the patient;
    a plurality of tubes, each tube having a proximal end and a distal end, with the distal end of each of the tubes being in sealed fluid communication with a corresponding cell, and the proximal end being in sealed fluid communication with a respective transducer external to the mouth piece, wherein each transducer is configured to convert changes in pressure within the cells to electrical signals;
    a processor for processing the electrical signals, wherein the electrical signals are modulated to generate a pressure profile from the cells representing a magnitude of pressure applied by the teeth as a function of time; and
    an electronics box external to the user's mouth for housing each transducer and the processor;
    wherein:
        the mouth piece further comprises a transition section extending from the arcuate portion of the mouth piece, the transition section having fluid channels corresponding to each fluid cell,
        each channel slidably receives a corresponding tube,
        the transition section is fabricated from a rigid thermoplastic material,
        the electronics box connects immediately to the transition section and is supported by the transition section and the tubes, and
        each tube slidably extends into the corresponding channel of the transition section.

2. The monitoring system of claim 1, wherein the electronics box comprises a data port for providing electrical communication with a computer monitor.

3. The mouth guard of claim 1, wherein the electronics box comprises a data port for providing electrical communication with a separate processor.

4. The mouth guard of claim 1, wherein:
    the electronics box comprises a manifold;
    each of the plurality of tubes comprises a jumper portion between a respective transducer and the manifold, and a mouth piece portion between the manifold and the mouth piece.

5. The monitoring system of claim 1, wherein:
    each cell and each tube contains (i) a compressible fluid, (ii) an incompressible fluid, or (iii) a combination thereof.

6. The monitoring system of claim 1, wherein:
    each cell and each tube contains a compressible fluid; and
    the compressible fluid comprises air, oxygen, carbon dioxide, nitrogen, argon, or combinations thereof.

7. The monitoring system of claim 1, wherein:
    each cell and each tube contains a non-toxic incompressible fluid; and
    the incompressible fluid comprises water.

8. The monitoring system of claim 1, wherein the mouth piece is fabricated from polyisoprene rubber, silicone, chloroprene rubber, neoprene, styrene butadiene rubber, acrylonitrile butadiene rubber, ethylene propylene diene methylene, polyvinylchloride, polyethylene, polyurethane, urethane-coated nylon, ethyl vinyl acetate, and combinations thereof.

9. The monitoring system of claim 1, wherein:
    the at least one fluid-containing cell on the left side comprises at least two cells, with one of the at least two cells being configured to be positioned between upper and lower molars; and
    the at least one fluid-containing cell on the right side comprises at least two cells, with one of the at least two cells also being configured to be positioned between upper and lower molars.

10. The monitoring system of claim 1, wherein:
    the at least one fluid-containing cell on the left side comprises a single cell; and
    the at least one fluid-containing cell on the right side also comprises a single cell.

11. The monitoring system of claim 1, wherein the processor receives electrical signals from each of the plurality of transducers and processes those signals such that each electrical signal represents a pressure reading from a corresponding cell.

12. The monitoring system of claim 1, wherein each of the plurality of tubes has an inner diameter of 0.05 inches to 0.5 inches.

13. The monitoring system of claim 1, wherein each of the plurality of tubes resides at a pressure of 15 psi to 30 psi.

14. The monitoring system of claim 11, wherein the pressure profile represents a magnitude of pressure within each separate cell as a function of time.

15. The monitoring system of claim 1, wherein each of the plurality of transducers is a pressure sensor having a diaphragm that is sensitive to changes in pressure within a tube.

16. The monitoring system of claim 15, wherein the electrical signals are voltage signals.

17. The monitoring system of claim 16, wherein each of the transducers comprises an analog-to-digital converter, such that the electrical signals are digital signal values.

18. The monitoring system of claim 1, wherein the processor receives each of the electrical signals, and (i) averages the individual signal values at specified time intervals to produce a separate pressure profile for each cell as a function of time, (ii) averages all signal values from the respective cells at specified time intervals to produce a single pressure profile as a function of time, or (iii) totals the signals from the cells at specified time intervals to produce a single pressure profile.

19. The monitoring system of claim 1, wherein each of the plurality of tubes comprises more than one tubular body operatively connected through a manifold to form individual, fluidically sealed channels.

20. The monitoring system of claim 1, further comprising:
    a transmitter designed to transmit wireless signals received from the processor, the signals representing the pressure profile generated by the processor.

21. A method for monitoring bite pressures of a patient during sleep, comprising:
    providing an elastomeric mouth piece comprising:
        opposing left and right sides, and an arcuate portion intermediate the left and right sides to form a horseshoe-shaped member;
        at least one fluid-containing cell residing within the mouth piece on the left side, and at least one fluid-containing cell residing within the mouth piece on the right side, the fluid-containing cells being configured to respond to pressure applied by the upper and lower teeth; and a plurality of tubes extending from the mouth piece, with each tube having a distal end in sealed fluid communication with a corresponding fluid-containing cell;
wherein:
each cell and each tube contains (i) a compressible fluid, (ii) a non-toxic incompressible fluid, or (iii) a combination thereof,
the mouth piece comprises a transition section extending from the arcuate portion of the mouth piece, and
the transition section is fabricated from a rigid thermoplastic material;
inserting each tube into a corresponding fluid channel residing in the transition section;
placing the mouth piece into a patient's mouth between upper and lower teeth of the patient;
having the patient sleep for a period of time with the mouth piece in the patient's mouth, wherein:
a proximal end of each of the plurality of tubes is in sealed fluid communication with a respective transducer external to the mouth piece, with each transducer being configured to convert changes in pressure within the cells to electrical signals,
the transducers are in electrical communication with a processor, with the processor being designed to process the electrical signals and to generate a pressure profile from the cells, and
the transducers and the processor are housed in an electronics box external to the mouth of the patient, with the electronics box being connected immediately to the transition sections; and
reviewing a graph that shows bite pressure exerted by the patient as a function of time.

22. The method of claim 21, wherein the electronics box comprises a port for providing electrical communication with a computer monitor.

23. The method of claim 21, wherein:
each cell and each tube contains a compressible fluid; and
the compressible fluid comprises air, oxygen, carbon dioxide, nitrogen, argon, or combinations thereof.

24. The method of claim 21, wherein:
each cell and each tube contains an incompressible fluid; and
the incompressible fluid comprises water.

25. The method of claim 21, wherein:
the at least one fluid-containing cell on the left side comprises at least two cells, with one of the at least two cells being positioned between upper and lower molars when the mouth piece is placed in a patient's mouth; and
the at least one fluid-containing cell on the right side comprises at least two cells, with one of the at least two cells also being positioned between upper and lower molars when the mouth piece is placed in the patient's mouth.

26. The method of claim 21, wherein:
the at least one fluid-containing cell on the left side comprises a single cell; and
the at least one fluid-containing cell on the right side comprises a single cell.

27. The method of claim 21, wherein the pressure profile represents a magnitude of pressure within each individual cell as a function of time.

28. The method of claim 21, wherein the processor receives electrical signals from each of the plurality of transducers and processes those signals such that each electrical signal represents a pressure reading from a corresponding cell.

29. The method of claim 21, wherein the processor receives each of the electrical signals, and (i) averages the individual signal values at specified time intervals to produce a separate pressure profile for each cell as a function of time, (ii) averages all signal values from the respective cells at specified time intervals to produce a single pressure profile, or (iii) totals the signals from the cells at specified time intervals to produce a single pressure profile.

30. The method of claim 21, further comprising:
placing the plurality of tubes in fluid communication with the corresponding plurality of transducers.

31. The method of claim 21, further comprising:
recording the patient's heart rate, breathing rhythm, and sleep patterns simultaneously with monitoring bite pressures as part of cardio-respiratory monitoring.

32. The method of claim 21, wherein the electronics box further comprises a transmitter, and the method further comprises:
wirelessly transmitting signals received from the processor to a transceiver, whereby the transceiver is associated with a monitor for displaying the pressure profile in real time.

33. The method of claim 21, further comprising:
uploading a digital file from the electronics box to a computer, the digital file containing the pressure profile of the patient.

34. The method of claim 33, further comprising:
synching the digital file with other medical data taken from the patient as a function of time.

35. The method of claim 21, wherein the electronics box further comprises a transmitter, and the method further comprises:
wirelessly transmitting signals received from the processor to a transceiver, whereby the transceiver stores the pressure profile into a digital file on a computer for later viewing by the patient or a health care provider.

36. The method of claim 35, wherein:
the processor receives each of the electrical signals, and (i) averages the individual signal values at specified time intervals to produce a separate pressure profile for each cell as a function of time, or (ii) averages all signal values from the respective cells at specified time intervals to produce a single pressure profile; and
compares the pressure profile to a designated pressure baseline for the patient.

37. An intra-oral system for monitoring bite pressures of a patient during sleep, the system comprising:
an elastomeric mouth piece dimensioned and configured to reside between the upper and lower teeth of a patient, the mouth piece comprising opposing left and right sides, and an arcuate portion intermediate the left and right sides to form a horseshoe-shaped member;
at least one fluid-containing cell residing within the mouth piece on the left side, and at least one fluid-containing cell residing within the mouth piece on the right side, the fluid-containing cells being configured to respond to pressure applied by the teeth of the patient;
a plurality of tubes, each tube having a proximal end and a distal end, with the distal end of each of the tubes being in sealed fluid communication with a corresponding cell, and the proximal end being in sealed fluid communication with a respective transducer external to the mouth piece, wherein each transducer is configured to convert changes in pressure within the cells to electrical signals;
a processor for processing the electrical signals, wherein the electrical signals are modulated to generate a pressure profile from the cells representing a magnitude of pressure as a function of time; and an electronics box for housing each transducer and the processor;

wherein:

the mouth piece further comprises a transition section extending from the arcuate portion of the mouth piece, the transition section having fluid channels corresponding to each fluid cell, with each channel being configured to receive the proximal end of a corresponding tube, the transition section is fabricated from a rigid thermoplastic material, the electronics box connects to is supported by the transition section and the tubes, and each tube slidably and frictionally extends into the corresponding channel of the transition section.

* * * * *